(12) United States Patent
Gwen

(10) Patent No.: US 7,090,687 B1
(45) Date of Patent: Aug. 15, 2006

(54) TONGUE CLEANER APPARATUS WITH AN ABRASIVE TABLET

(76) Inventor: Patrick Gwen, 1815 Edmundson, Houston, TX (US) 77003

( * ) Notice: Subject to any disclaimer, the term of this patent is extended or adjusted under 35 U.S.C. 154(b) by 411 days.

(21) Appl. No.: 10/713,464

(22) Filed: Nov. 17, 2003

Related U.S. Application Data

(63) Continuation-in-part of application No. 10/440,297, filed on May 19, 2003.

(51) Int. Cl.
*A61B 17/24* (2006.01)
(52) U.S. Cl. .................................................... 606/161
(58) Field of Classification Search ................ 606/161; 601/137; 15/106–111; 433/91
See application file for complete search history.

(56) References Cited

U.S. PATENT DOCUMENTS

| 5,735,864 | A | | 4/1998 | Heisinger, Jr. |
| 6,083,003 | A | * | 7/2000 | Kwasnik et al. ............... 433/91 |
| 2003/0163149 | A1 | * | 8/2003 | Heisinger ..................... 606/161 |
| 2004/0152031 | A1 | * | 8/2004 | Takahashi ....................... 433/1 |

* cited by examiner

*Primary Examiner*—Vy Bui
(74) *Attorney, Agent, or Firm*—Egbert Law Offices

(57) ABSTRACT

A tongue cleaner apparatus having a elongate body with a gripping area at one end thereof and a tablet receiving area adjacent an opposite end thereof, a cleaning edge formed at the opposite end of the elongate body, and a tablet affixed within the tablet receiving area of the elongate body. The tablet has a plurality of protrusions or a plurality of indentations on a surface of the tablet. The protrusions or indentations extend from the surface of the tablet that contacts the tongue. The tablet increases the abrasiveness and surface area of contact on the tongue.

17 Claims, 4 Drawing Sheets

TONGUE CLEANER APPARATUS WITH AN ABRASIVE TABLET

RELATED U.S. APPLICATIONS

The present application is a continuation-in-part of U.S. patent application Ser. No. 10/440,297 filed on May 19, 2003, and entitled "TONGUE CLEANER APPARATUS", presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to devices for the cleaning of mouths and dental areas. More particularly, the present invention relates to tongue cleaning devices which employ physical and chemical processes simultaneously for the cleaning of the tongue and mouth to remedy bad breath.

BACKGROUND OF THE INVENTION

Tongue cleaning is carried out in many areas of the world for the cleaning of mouth and dental areas. In particular, the cleaning of tongues is carried out so as to remove volatile sulfur compounds. This accumulation of bacteria is the most common cause of bad breath, affecting up to 85% of halitosis sufferers. Tongue cleaning is recommended by the American Dental Association and dental professionals nationwide for the treatment of chronic halitosis.

FIGS. 1 and 2 show a prior art tongue cleaner device known as the SAKOOL (™) tongue cleaner device. This tongue cleaner device 10 is illustrated, with particularity, in FIG. 1. The tongue cleaner device 10 includes a flexible strip 12 which is suitable for conforming to the surface of the tongue for quick and easy cleaning. The strip 12 has a narrow width for avoiding the gag reflex. The strip 12 can be spearmint or cinnamon scented. FIG. 2 shows the tongue cleaner device 10 as utilized for the cleaning of the tongue 14 of person 16. As can be seen, the ends 18 and 20 are gripped by the fingers 22 of person 16. The ends 18 and 20 are bent toward each other so as to form an internal region 24. The tongue 14 is then stuck out of the mouth 26 of person 16 so as to enter the interior area 24 of the device 10. The bottom edge of the strip 12 will then pass over the upper surface of the tongue 14 so as to effectively scrape the tongue of person 16. Following the use, the tongue cleaner device 10 can be washed off and reused again. This prior art tongue cleaner is a purely physical process involving direct contact between the edge of the strip and the surface of the tongue.

U.S. Pat. No. 5,735,864, issued on Apr. 7, 1998 to C. G. Heisinger, Jr., teaches a disposable oral-hygiene instrument for loosening, collecting, and removing debris from the surface of the tongue. The device has a handle at one end with a textured surface at the other end for scrubbing the dorsal surface of the tongue. Along the distal perimeter edge of the scrubbing surface extends a cleaner for removing debris from the back to the front of the tongue. An absorbent material for collecting and removing debris is affixed to the same end of the instrument as the scrubbing surface. Although this device can be effective for the scrubbing of tongues, it requires extra manufacturing operations and is relatively expensive. A flavoring is applied to the scrubbing surface so as to minimize the gag reflects. However, the adding of flavoring to the roughened scrubbing surface will tend to reduce the impact and effect of the scrubbing surface. The scrubbing surface has a plurality of molded bumps formed thereon. In conventional injection molding procedures, these bumps will have a considerable size in order to have a cavity formed of metal in the injection molding machine. This device also lacks suitable openings for facilitating saliva circulation over and around the flavored surface and the scrubbing surface.

It is an object of the present invention to provide a tongue cleaning apparatus which employs both physical and chemical processes for the cleaning of the tongue.

It is another object of the present invention to provide a tongue cleaning apparatus which deposits an aesthetic-type mint flavoring and antiseptic solution onto the tongue of the user.

It is still another object of the present invention to provide a tongue cleaner apparatus which uses a flavored tablet for the purpose of providing a scrubbing action in both a micro- and macro-textured manner.

It is a further object of the present invention to provide a tongue cleaner apparatus with increased surface area contact between the tablet and the tongue.

It is another object of the present invention to provide a tongue cleaner apparatus with improved abrasive contact between the tablet and the tongue.

It is still a further object of the present invention to provide a tongue cleaner apparatus which is easy to manufacture, easy to use, and relatively inexpensive.

These and other objects and advantages of the present invention will become apparent from a reading of the attached specification and appended claims.

BRIEF SUMMARY OF THE INVENTION

The present invention is a tongue cleaner apparatus having a elongate body with a gripping area at one end thereof and a tablet receiving area adjacent an opposite end thereof, a cleaning edge formed at the opposite end of the elongate body, and a tablet affixed within the tablet receiving area of the elongate body. The tablet has a plurality of protrusions or indentations on a surface of the tablet.

In the present invention, the tablet is dissolvable upon contact with human saliva. This tablet has a plurality of protrusions or indentations or a mixture thereof on the surface of the tablet that contacts the tongue. The protrusions are convex, and the indentations are concave. The convex protrusions extend outwardly from the surface of the tablet to contact the tongue. The concave indentations extend inwardly from the surface of the tablet to create a roughened surface of the tablet. The tablet has one side secured to the tablet receiving area and an opposite side positioned outwardly of a rim of the tablet receiving area. The cleaning edge extends downwardly from the opposite end of the elongate body for a distance less than the distance that the tablet extends downwardly from the tablet receiving area of the elongate body.

The tablet can be of multiple forms, including mint flavorings and other flavorings incorporated therein. The tablet can be of multiple layers, such as having a soft outer surface and a roughened inner surface. The tablet improves abrasive scrubbing action for both macro and micro surfaces of the tongue by mechanical action of the protrusions or indentations. The tablet also increases contact with the tongue with more surface area contact. Furthermore, as the tablet dissolves, the circular tablet holder edge will provide additional tongue scraping surfaces. The circular tablet holder edge maximizes surface area contact with the tongue.

In the present invention, the elongate body and the cleaning edge are integrally formed together of a polymeric material.

BRIEF DESCRIPTION OF THE SEVERAL VIEWS OF THE DRAWINGS

FIG. 7A shows convex protrusions, and FIG. 7B shows concave protrusions.

DETAILED DESCRIPTION OF THE INVENTION

Figure 1:
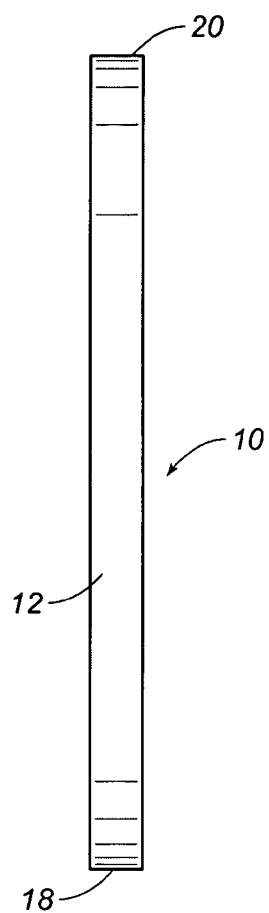
FIG. 1 is a plan view of the prior art tongue cleaner apparatus.
Figure 2:
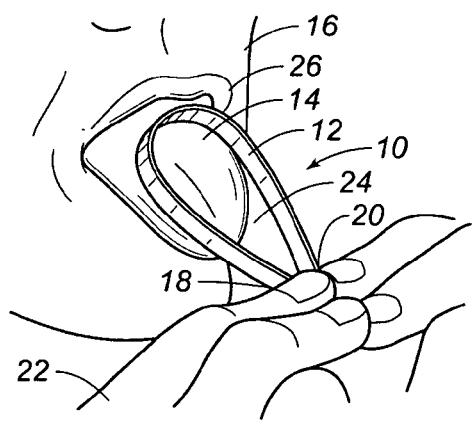
FIG. 2 is an illustration showing the use of the prior art tongue cleaner apparatus of FIG. 1.
Figure 3:
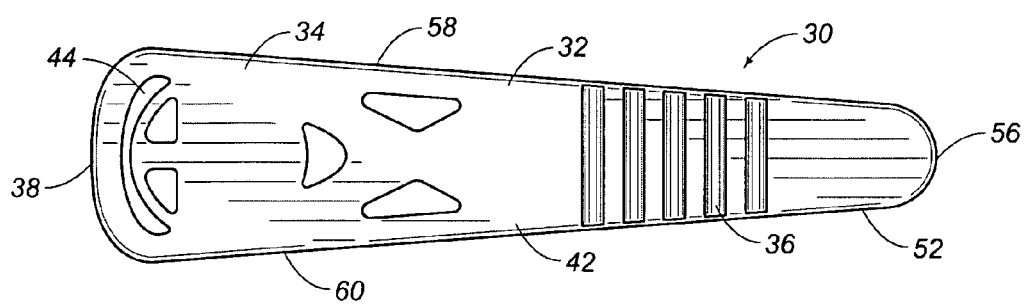
FIG. 3 is a plan view of the tongue cleaner apparatus of the present invention.

Referring to FIG. 3, there is shown the tongue cleaner apparatus 30 in accordance with the teachings of the present invention. FIG. 3 shows a plan view of the tongue cleaner apparatus 30 of the present invention. The tongue cleaner apparatus 30 includes an elongate body 32 having a tablet-receiving area 34 formed at one end of the elongate body 32 and a gripping area 36 formed at an opposite end of the elongate body 32. A cleaning edge 38 is formed at an end of the elongate body 32 opposite the gripping area 36. A tablet 40 is affixed within the tablet-receiving area 34 of the elongate body 32. The tablet 40 has a plurality of protrusions (not shown in the plan view of FIG. 3) on a surface thereof. The tablet 40 is positioned inwardly of the cleaning edge 38 and directly below an orifice 44 formed inwardly of the cleaning edge 38.

As can be seen in FIG. 3, the elongate body 32 is formed by the planar surface 42 and a rim 52 extending around the periphery of the planar surface 42. As will be shown in later drawings, the rim 52 extends downwardly around the periphery of the planar surface 42 so as to provide structural integrity to the elongate body 32. The end 56 of the elongate body 32 is suitably curved.

The cleaning edge 38 is formed at the end of the elongate body 32 opposite the end 56. The cleaning edge 38 is also curved between the sides 58 and 60 of the elongate body 32. The orifice 44 is positioned just behind the cleaning edge 38 and above the tablet 40. Orifice 44 facilitates the flow of saliva in circulation around the tablet 40.

Figure 4:
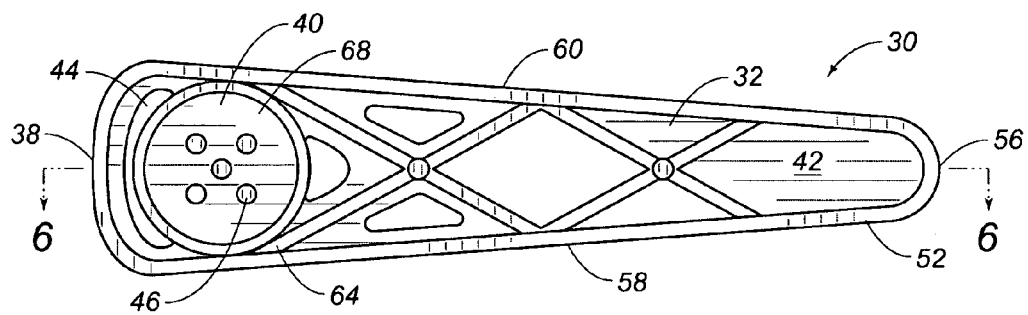
FIG. 4 is a bottom view of the tongue cleaner apparatus of the present invention.

In FIG. 4, it can be seen that the tablet 40 is positioned within a tablet receiving area 64 formed on the underside of the planar surface 42. There are a plurality of protrusions 46 on a surface of the tablet 40. A portion of the tablet 40 resides directly below the orifice 44 and inwardly of the cleaning edge 38. Within the concept of the present invention, a plurality of indentations can be substituted for the plurality of protrusions. Additionally, with the concept of the present invention, a mixture of protrusions and indentations can be formed on the surface of the tablet.

In FIG. 4, it can be seen that the cleaning edge 38 is actually a portion of the rim 52. The cleaning edge 38 extends downwardly from the planar surface 42. The cleaning edge 38 is slightly spaced from the adjacent edge of the tablet 40. The cleaning edge 30 extends between the sides 58 and 60 of the elongate body 32.

When the cleaning edge 38 is placed against the surface of the tongue, the tablet 40 will come into contact with tongue. Since the tablet 40 is dissolvable upon contact with human saliva, the tablet 40 will slightly dissolve so as to release an anaesthetic-type flavoring and its anti-gag reflex sweetener. The cleaning edge 38 is moved backward and forward across the top surface of the tongue. As the cleaning action occurs, the tablet 40 will continue to release its flavoring, its sweetener, and its anti-bacterial agent. The present invention provides a physical and chemical process for the cleaning of the tongue. The cleaning action caused by the cleaning edge 38 will produced the benefits caused by tongue cleaning, as described herein previously. Furthermore, as the tablet dissolves, the circular tablet holder edge will provide additional tongue scraping surfaces. The circular tablet holder edge maximizes surface area contact with the tongue.

Figure 5:
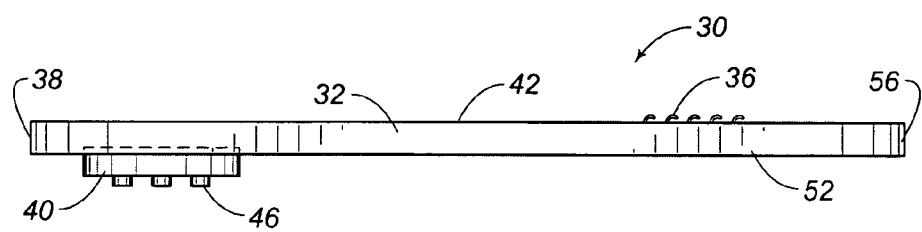
FIG. 5 is a side elevational view of the tongue cleaner apparatus of the present invention.

FIG. 5 shows a side elevational view of the apparatus 30 of the present invention showing, in particular, the rim 52 as extending downwardly from the planar surface 42 of the elongate body 32. The elongate body has curved ends 56 and 38. Importantly, in FIG. 5, it can be seen that the tablet 40 extends downwardly from the planar surface 42 for a greater distance than does the cleaning edge 38. As a result, initial contact between the tongue cleaning apparatus 30 and the tongue will be from the surface of the tablet 40.

Figure 6:
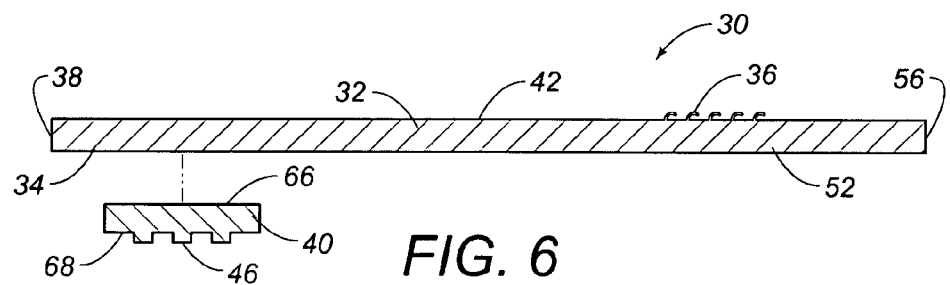
FIG. 6 is cross-sectional view taken across line 6—6 of FIG. 4 of the tongue scraper apparatus of the present invention showing the tablet in exploded form.

FIG. 6 shows a cross-sectional view of the tongue cleaner apparatus 30 of the present invention. The tablet 40 is illustrated in exploded fashion suitable for securement within the tablet receiving area 34 of the planar surface 42 of elongate body 32. The tablet 40 can have a suitable adhesive 66 applied to a top surface thereof. The opposite surface 68 of tablet 40 will be the surface with the plurality of protrusions which contacts the surface of the human tongue.

In FIG. 6, it can be seen that the cleaning edge 38 extends downwardly from the end of the planar surface 42. The cleaning edge 38 is simply a portion of the downwardly extending rim 52. As a result, the present invention can be suitably manufactured in an injection molding process. The elongate body 32 can be integrally formed of a polymeric material. The tablet 40 can then be adhesively secured within the tablet receiving area 34 in a simple and convenient manner.

In the present invention, the tablet 40 can have a wide variety of configurations as shown in FIGS. 7A–7B, FIGS. 8A–8B and FIGS. 9A–9B. The surface 68 of the tablet 40 should have a suitable abrasive property from the plurality of protrusions or indentations 46 so as to affect the micro and macro surfaces of the tongue. As the tablet 40 brushes across the tongue, the protrusions or indentations 46 will contact the tongue and will tend dispense flavoring and other anaesthetic materials onto the tongue. The protrusions or indentations 46 will also provide a roughened abrasive surface for improved scrubbing action provided to the tongue. Furthermore, the protrusions or indentations 46 expose more surface area of the tablet 40 to contact the tongue. The tablet 40 can be adhered within the tablet receiving area 34 by suitable adhesives.

Figure 7A:
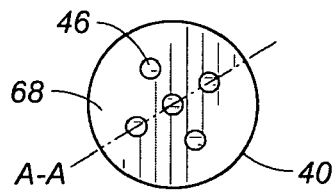
FIGS. 7A–7B are bottom views of the tablet of the tongue cleaner apparatus of the present invention.
Figure 7B:
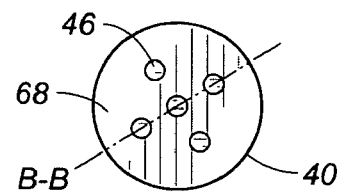
Figure 8A:
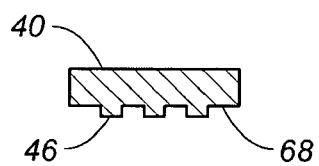
FIGS. 8A–8B are cross-sectional views taken across lines A—A and B—B respectively of FIGS. 7A–7B of the tablet of the tongue cleaner apparatus of the present invention.
Figure 8B:
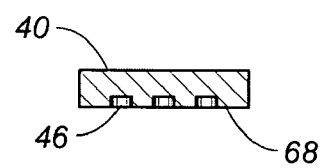

In the preferred embodiment, FIGS. 7A and 8A show the plurality of protrusions 46 as convex, extending from the surface 68 of the tablet 40. Saliva will freely flow around the convex protrusions 46 on the surface 68 as any textured surface. The protrusions 46 are shown in a staggered formation, centered on the tablet surface 68. The five individual protrusions 46 have one protrusion 46 centered in the middle of the tablet, with the remaining four protrusions evenly spaced in a quadrant surrounding the center protrusion to form the staggered formation. FIGS. 7B and 8B show the plurality of indentations 46 as concave, extending inwardly from the surface 68 of the tablet 40. The concave indentations 46 act as pits to form the abrasive surface, and the edges of the concave indentations form scraping surface area to the tongue. Similar to FIGS. 7A and 8A, the pattern of the five indentations 46 include a single centered indentation with the remaining four indentations evenly spaced in quadrants around the center indentation. Alternative spatial arrangements of the protrusions or indentations 46, such as circular, polygonal or linear, are within the scope of the present invention.

An embodiment of the present invention can also include a mixture of protrusions and indentations 46 across the surface 68 of the tablet 40. The mixture will increase the abrasiveness of the tablet, having scraping surfaces created by both protrusions extending outwardly and indentations creating edges into the surface of the tablet. The mixture of protrusions and indentations also achieves the objectives of the preferred embodiment.

In FIGS. 7A–7B and 8A–8B, the plurality of protrusions 46 are shown as columnar in shape. The edges on the surface 68 are rounded by the circular columns of the protrusions or indentations 46. A planar top of each protrusion or a planar bottom of each indentation are shown in the figures. In both sets of figures, the abrasive surface of the tablet 40 of the present invention has increased roughness for scrubbing action and more surface area to contact the tablet 40 and the tongue.

Figure 9A:
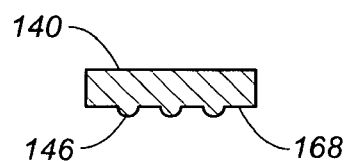
FIGS. 9A–9B are cross-sectional views taken across lines A—A and B—B, respectively of FIGS. 7A–7B showing an alternative embodiment of the tablet of the tongue cleaner apparatus of the present invention.
Figure 9B:
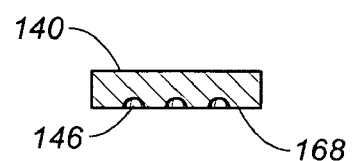

FIGS. 9A–9B are alternative embodiments of the tablet 140 of the present invention. In particular, the plurality of protrusions or indentations 146 are semispherical in shape. The protrusions or indentations 146 extend from a surface 168 of the tablet 140. The same increase in abrasive property and surface area against the tongue are achieved by this embodiment of the present invention. The protrusions 146 in FIG. 9A increase the surface area contact with the tongue, and the indentations 146 in FIG. 9B create the same scrubbing edges to improve the abrasive property of the tablet 140. Additional shapes of the protrusions and indentations 146 are within the concept of the present invention.

The tablet 40 can be a pill, a deposit of material, a lozenge, or other item which is dissolvable upon contact with human saliva. The tablet 40 can include a suitable anaesthetic-type flavoring and can also include a sweetening agent. An anti-bacterial agent can also be incorporated into the tablet 40. As the tablet 40 becomes dissolved from contact with human saliva, micro-pits and micro-bumps will form on the surfaces of the tablet 40 and protrusions or indentations 46. These micro-pits and micro-bumps will tend dispense flavoring and other anaesthetic materials onto the tongue. Similarly, the micro-pits and micro-bumps will provide another additional roughened textured surface for the scrubbing action provided to the tongue. In one embodiment, the anaesthetic-type flavoring can be a mint flavoring or other agent which temporarily deadens the feeling on the surface of the tongue. The sweetener can be sugar or other agents which serves to suppress the gag reflex.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A tongue cleaner apparatus comprising:
   an elongate body with a gripping area at one end and a tablet receiving area adjacent an opposite end;
   a cleaning edge formed at said opposite end of said elongate body and extending downwardly from said elongate body;
   a tablet affixed within said tablet receiving area of said elongate body and extending downwardly from said elongate body, said tablet having a plurality of protrusions or a plurality of indentations on a surface of said tablet;
   said tablet having one end secured to an underside of said tablet receiving area of said elongate body; and
   said surface of said tablet positioned downwardly further from said cleaning edge.

2. The apparatus of claim 1, said tablet being dissolvable upon contact with human saliva.

3. The apparatus of claim 1, said plurality of protrusions being convex.

4. The apparatus of claim 1, said plurality of indentations being concave.

5. The apparatus of claim 3, said plurality of protrusions extending outwardly from said surface.

6. The apparatus of claim 4, said plurality of indentations extending inwardly of said surface.

7. The apparatus of claim 1, said cleaning edge extending downwardly from said opposite end of said elongate body for a distance less than a distance that said tablet extends downwardly from said tablet receiving area.

8. A tongue cleaner apparatus comprising:
   an elongate body having a generally planar surface having a cleaning edge extending downwardly from said planar surface adjacent one end of said elongate body, said elongate body having an orifice formed through said planar surface adjacent said cleaning edge;
   a tablet affixed to an underside of said elongate body adjacent said cleaning edge, said tablet having a plurality of protrusions or a plurality of indentations extending from a surface of said tablet opposite said planar surface;
   said elongate body having a rim extending downwardly around at least a portion of a periphery of said planar surface and defining said cleaning edge; and
   said tablet extending downwardly from said planar surface for a distance greater than a distance that said cleaning edge extends downwardly from said planar surface.

9. The apparatus of claim 8, said tablet having a portion positioned directly below said orifice.

10. The apparatus of claim 8, said tablet being dissolvable upon contact with human saliva.

11. The apparatus of claim 8, said plurality of protrusions being columnar.

12. The apparatus of claim 8, said plurality of protrusions being semi-spherical.

13. A tongue cleaner apparatus comprising:
- an elongate body having a generally planar surface with a rim extending downwardly therefrom around at least a portion of a periphery of said planar surface, said elongate body having an orifice formed through said planar surface generally adjacent one end of said elongate body;
- a tablet affixed to an underside of said elongate body adjacent said one end of said elongate body, said tablet having a plurality of protrusions or a plurality of indentations extending from a surface of said tablet opposite said planar surface of said elongate body;
- said elongate body having a cleaning edge extending downwardly from said planar surface adjacent said one end of said elongate body, said tablet positioned adjacent said cleaning edge; and
- said cleaning edge extending downwardly from said planar surface of said elongate body for a distance less than a distance that said tablet extends downwardly from said planar surface.

14. The apparatus claim 13, said plurality of protrusions being columnar.

15. The apparatus of claim 13, said plurality of protrusions being semispherical.

16. The apparatus of claim 13, said tablet being dissolvable upon contact with human saliva.

17. The apparatus of claim 13, said tablet having a portion positioned directly below said orifice.

* * * * *